US00PP29558P3

(12) United States Plant Patent
Van Swieten

(10) Patent No.: US PP29,558 P3
(45) Date of Patent: Jul. 31, 2018

(54) ***PHALAENOPSIS* ORCHID PLANT NAMED 'PHALFLAJ'**

(50) Latin Name: ***Phalaenopsis* hybrid**
Varietal Denomination: PHALFLAJ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 112 days.

(21) Appl. No.: 15/330,063

(22) Filed: Aug. 1, 2016

(65) Prior Publication Data

US 2018/0035594 P1 Feb. 1, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

UPOV-PLUTO: Plant Variety Database, citation for 'PHALDFLAJ'; Internet retrieval Sep. 25, 2017.*
EU Community Plant Variety Rights Application No. 2016/0959, Application n°A201600647, filed Apr. 18, 2016, 8 pages.
EU Community Plant Variety Office Official Gazette, Mar. 2016, Jun. 15, 2016, cover page and pp. 35, 52.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFLAJ', particularly characterized by having small, white flowers, 1 to 4 peduncles that are short and sturdy, leaves that are oblong, and is propagated by meristem tissue culture, is disclosed.

3 Drawing Sheets

Genus and species: *Phalaenopsis* hybrid.
Variety denomination: 'PHALFLAJ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFLAJ'.

The new *Phalaenopsis* plant is a product of a planned breeding program conducted by the inventor in Bleiswijk, The Netherlands. The objective of this breeding program was to create a new *Phalaenopsis* plant with numerous branches and attractive small white flowers, suitable for potted plant production.

The new *Phalaenopsis* plant 'PHALFLAJ' is a result of cross-pollination made by the inventor in October 2005 in Bleiswijk, The Netherlands of the proprietary female, or seed parent, *Phalaenopsis* hybrid '11968-04' (unpatented) with the proprietary male, or pollen parent, *Phalaenopsis* hybrid '23266-02' (unpatented).

The new *Phalaenopsis* was selected by the inventor as a single plant within the progeny of the stated cross-pollination in a controlled greenhouse in Bleiswijk, The Netherlands in June 2009. Asexual reproduction of the new *Phalaenopsis* plant by meristem tissue culture since March 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALFLAJ' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFLAJ' as a new and distinct variety of *Phalaenopsis* plant.

1) Small, white flowers;
2) 1 to 4 peduncles;
3) Peduncle is short and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in April 2016. Colors in the photographs may differ from the color values cited in the detailed botanical description, which accurately describe the actual colors of the new variety.

DESCRIPTION OF THE NEW VARIETY

Figure 1:
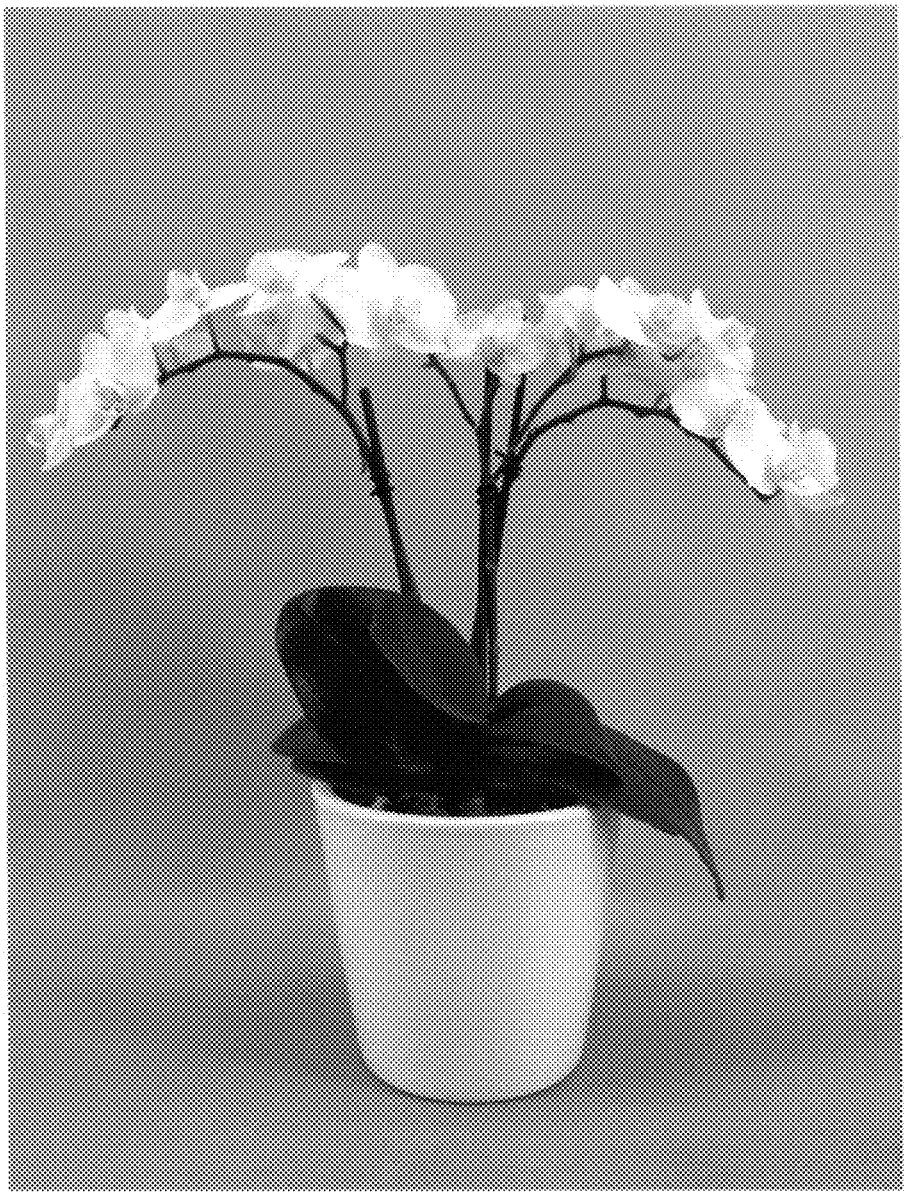
FIG. 1 shows the overall plant habit, including blooms and foliage of 'PHALFLAJ'.
Figure 2:
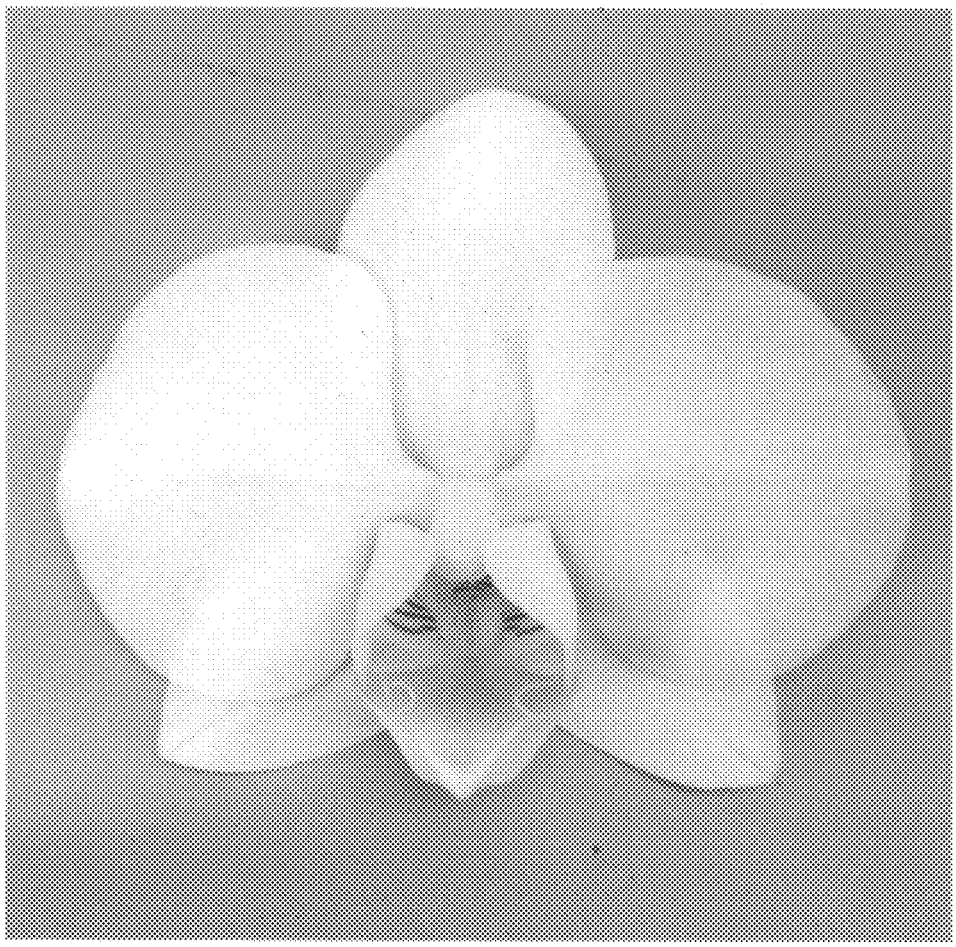
FIG. 2 shows a close-up of a flower of 'PHALFLAJ'.
Figure 3:
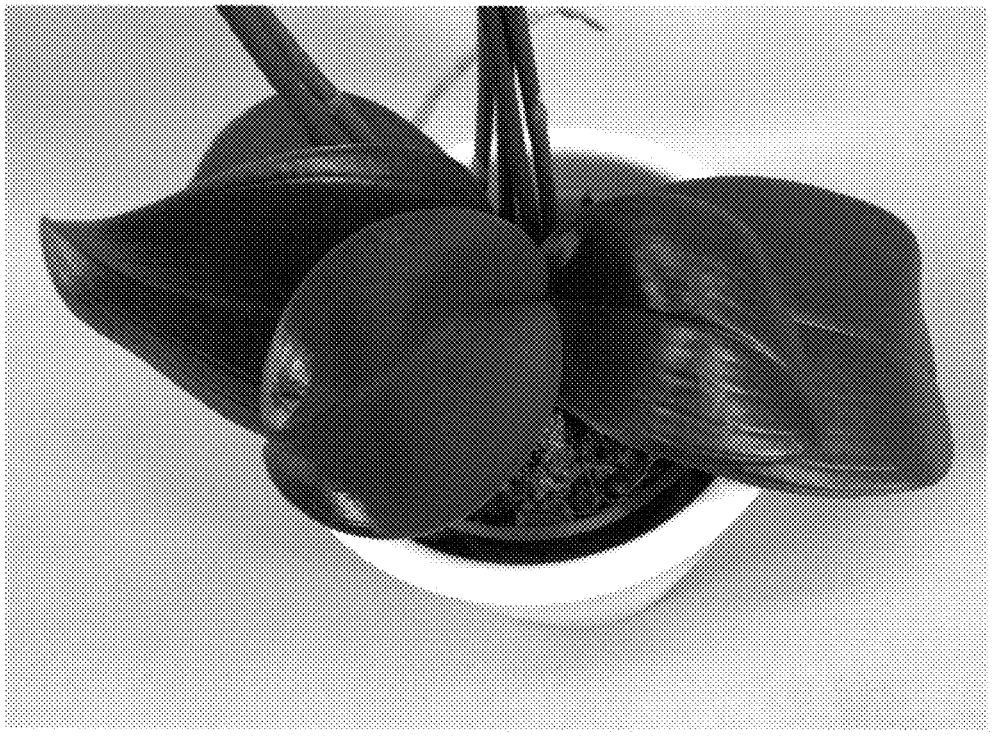
FIG. 3 shows a close-up of the leaves of 'PHALFLAJ'.

The following detailed description sets forth the distinctive characteristics of 'PHALFLAJ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in April 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALFLAJ'.

Parentage:
- *Female parent*.—*Phalaenopsis* cultivar '11968-04' (unpatented).
- *Male parent*.—*Phalaenopsis* cultivar '23266-02' (unpatented).

Propagation:
- *Type*.—Meristem tissue culture.

Roots:
- *Root description*.—Greyed-green colored roots with branching lateral roots having light purple and light green colored root tips.

Plant:
- *Commercial crop time to flowering*.—Approximately 48 to 50 weeks from a rooted cutting to finish in a 12 cm pot.
- *Growth habit of peduncle*.—Standard, green leaves and panicle.
- *Height (from soil level to top of inflorescence)*.—Approximately 26.0 cm to 36.0 cm.
- *Width (measured from leaf tips)*.—About 17.0 cm to 21.0 cm.
- *Vigor*.—Strong.

Leaves:
- *Mature leaves*.—Quantity per plant: 8 to 10 leaves are produced before flowering. Length (fully expanded): 12.0 cm to 15.0 cm. Width: 8.0 cm to 9.0 cm. Shape: Oblong. Base shape: Slightly elongated. Apex: Rounded unequal. Leaf blade angle with the petiole (measured from the horizontal position): Between 0 degrees and 25 degrees. Leaf margin: Entire. Color: Upper surface: RHS NN137B. Lower surface: RHS 146A. Texture: Smooth. Thickness: 2.0 mm to 2.3 mm. Venation: Pattern: Parallel. Color of the midvein: Upper surface: RHS 147A. Lower surface: RHS 146A.

Peduncle:
- *Quantity per plant*.—1 to 4.
- *Number of flowers per peduncle*.—14 to 23.
- *Length*.—26.0 cm to 36.0 cm.
- *Diameter*.—4.1 mm to 4.3 mm.
- *Strength*.—Strong.
- *Aspect*.—Upright.
- *Texture*.—Smooth.
- *Color*.—Green (RHS 146A) with a touch of dark purple (RHS 187A).
- *Internode length*.—3.5 cm to 4.5 cm.
- *Callosities*.—None.

Inflorescence description:
- *Appearance*.—Upright to slightly pendant, panicle inflorescence with bilaterally symmetrical flowers that open in succession beginning with the lowermost flower.
- *Inflorescence size*.—Height (from base to tip): 120.0 mm to 140.0 mm.
- *Flowering time*.—First flowers can be expected 10 to 11 months after planting in a 12 cm (diameter) pot.
- *Flower*.—Height: 59.0 mm to 61.0 mm. Diameter: 62.0 mm to 64.0 mm. Depth of lip: 15.0 mm to 17.0 mm.
- *Flower longevity*.—On the plant: 5 to 8 weeks.
- *Fragrance*.—Absent.
- *Flower bud*.—Average size: Medium. Length: 16.0 mm to 18.0 mm. Width: 13.0 mm to 15.0 mm. Shape: Egg shaped. Color: Green (RHS N144D).
- *Petals*.—Arrangement: Open/free. Shape: Semi-circular. Apex: Rounded asymmetric. Margin: Entire. Length (from base to tip): 28.0 mm to 30.0 mm. Width: 34.0 mm to 36.0 mm. Color (when fully opened): Upper surface: Basic color: White (RHS NN155C). Over color: Absent. Lower surface: Basic color: White (RHS NN155C). Over color: Absent.
- *Dorsal sepal*.—Shape: Elliptic. Apex: Obtuse symmetric. Margin: Entire. Length (from base to tip): 31.0 mm to 33.0 mm. Width: 22.0 mm to 24.0 mm. Color (when fully opened): Upper surface: Basic color: White (RHS NN155C). Over color: Absent. Lower surface: Basic color: White (RHS NN155C). Over color: Absent.
- *Lateral sepals*.—Shape: Ovate. Apex: Obtuse asymmetric. Margin: Entire. Length (from base to tip): 31.0 mm to 33.0 mm. Width: 18.0 mm to 20.0 mm. Color (when fully opened): Upper surface: Basic color: White (RHS NN155C). Over color: Absent. Lower surface: Basic color: White (RHS NN155C). Over color: Light green (RHS 145D).
- *Labellum (lip)*.—Margin: Entire. Whiskers: Present. Length of whiskers: 12.0 mm to 14.0 mm. Color of whiskers: White (RHS NN155C). Pubescence on the lip: Absent.
- *Lateral lobe*.—Shape: Spatulate. Length (from base to tip): 16.0 mm to 18.0 mm. Width: 10.0 mm to 12.0 mm. Color: White (RHS NN155C) and slightly green (RHS 150B) on one side with a few purple (RHS 187C) stripes towards the base.
- *Apical lobe*.—Shape: Triangular. Length: 14.0 mm to 16.0 mm. Width: 17.0 mm to 19.0 mm. Color: White (RHS NN155C) with green (RHS 150B) towards the callus.
- *Callus*.—Average size: Small to medium. Height: 0.5 cm to 0.7 cm. Length: 0.3 cm to 0.5 cm. Width: 0.2 cm to 0.4 cm. Color: Yellow (RHS 12B) and dotted.

*Reproductive organs*.—Column: Length: 7.0 mm to 9.0 mm. Diameter: 4.0 mm to 4.2 mm. Color: White (RHS NN155C). Pollinia: Quantity: 2. Diameter: 0.9 mm to 1.1 mm. Color: Yellow-orange (RHS 23A). Ovary: Length: 7.0 mm to 9.0 mm. Diameter: 2.0 mm to 2.2 mm. Pedicel: Length: 29.0 mm to 31.0 mm. Diameter: 2.2 mm to 2.5 mm. Color: Green (RHS NN137B) and light green (RHS 144D) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

'PHALFLAJ' differs from female parent plant '11968-04' (unpatented) in that 'PHALFLAJ' has a small to medium callus, darker green peduncles with a touch of dark purple, a rounded petal apex, and a striped lateral lobe, whereas '11968-04' has a medium callus, lighter green peduncles, an obtuse petal apex, and a striped and dotted lateral lobe. Additionally, 'PHALFLAJ' has longer petals and whiskers than '11968-04'.

The male parent of 'PHALFLAJ', cultivar '23266-02' (unpatented), is no longer in existence, so a meaningful comparison cannot be made.

'PHALFLAJ' is most similar to the commercial *Phalaenopsis* plants named 'PHALBAPAK' (U.S. Plant Pat. No. 27,508) and 'PHALDUXI' (U.S. Plant Pat. No. 25,680). 'PHALFLAJ' differs from the commercial variety 'PHALBAPAK' in that 'PHALFLAJ' has lateral sepals with no over color and dorsal sepal lower surfaces with no over color, whereas 'PHALBAPAK' has lateral sepals with light green and light purple over color towards the apex, and dorsal sepal lower surfaces with light purple and yellow-green over color. Additionally, 'PHALFLAJ' has shorter petals than 'PHALBAPAK'.

'PHALFLAJ' differs from the commercial variety 'PHALDUXI' in that 'PHALFLAJ' has lateral sepals with even coloring at the base and a rounded petal apex, whereas 'PHALDUXI' has lateral sepals with dots/spots at the base and a mucronate petal apex. Additionally, 'PHALFLAJ' has longer petals than 'PHALDUXI'.

I claim:

1. A new and distinct variety of *Phalaenopsis* plant named 'PHALFLAJ', substantially as described and illustrated herein.

* * * * *